(12) United States Patent
Allphin et al.

(10) Patent No.: US 8,869,800 B2
(45) Date of Patent: Oct. 28, 2014

(54) ADJUSTABLE TONGUE-POSITIONING DEVICE FOR SURGICAL GAG

(71) Applicant: Mercy Medical Research Institute, Springfield, MO (US)

(72) Inventors: Allan Allphin, Springfield, MO (US); Martin Reuter, Flemington, MO (US); Rahul Eapen, Monett, MO (US)

(73) Assignee: Mercy Medical Resesarch Institute, Springfield, MO (US)

( * ) Notice: Subject to any disclaimer, the term of this patent is extended or adjusted under 35 U.S.C. 154(b) by 75 days.

(21) Appl. No.: 13/775,748

(22) Filed: Feb. 25, 2013

(65) Prior Publication Data

US 2013/0220345 A1    Aug. 29, 2013

Related U.S. Application Data

(60) Provisional application No. 61/602,947, filed on Feb. 24, 2012.

(51) Int. Cl.
*A61C 5/14* (2006.01)

(52) U.S. Cl.
USPC ........................................ 128/859; 128/860

(58) Field of Classification Search
USPC .................... 128/848, 859–862; 600/205, 239
See application file for complete search history.

(56) References Cited

U.S. PATENT DOCUMENTS

| | | | | |
|---|---|---|---|---|
| 1,388,421 A | * | 8/1921 | Forgrave | 600/239 |
| 1,420,493 A | * | 6/1922 | Moyer | 600/239 |
| 2,476,675 A | | 12/1945 | McIvor | |
| 2,756,742 A | | 7/1956 | Barton | |
| 2,947,305 A | * | 8/1960 | Storz | 600/239 |
| 3,154,069 A | * | 10/1964 | Ring | 600/205 |
| 3,550,584 A | * | 12/1970 | Ring | 600/205 |
| 4,064,873 A | | 12/1977 | Swenson | |
| 4,213,451 A | | 7/1980 | Swenson | |
| 4,425,909 A | | 1/1984 | Rieser | |
| 5,024,218 A | | 6/1991 | Ovassapian et al. | |
| 7,887,483 B2 | | 2/2011 | Rosenberg | |
| 2008/0319270 A1 | | 12/2008 | Rosenberg | |
| 2010/0095968 A1 | | 4/2010 | Ogilvie et al. | |

OTHER PUBLICATIONS

McCarth, "Outpatient Anesthesia," Jacksonville Medicine, Dec. 1998, 7 pages.
Broyles, "Tonsillectomy and Adenoidectomy Rates in the United States," Edited and published by LA Zaykoski on Apr. 29, 2009; Healthguideinfo.com; http://www.healthguideinfo.com/ear-nose-throat/p33464/.

(Continued)

*Primary Examiner* — Michael A. Brown
(74) *Attorney, Agent, or Firm* — Lathrop & Gage LLP

(57) ABSTRACT

An adjustable tongue-positioning device for an oral gag device has a shaft portion with a vertical shaft adapted for slideably engaging with an oral gag device, an engagement bead attached to a support, the support attached to the vertical shaft, an engagement ring attached to the vertical shaft. The tongue positioning device also has an adjustable tongue portion with at least one tongue depressor portion having a slot adapted for engaging with the engagement bead of the shaft portion, and a flexible ratchet adapted for engaging with the engagement ring of the shaft portion. In operation the adjustable tongue portion is engaged with the engagement ring and bead of the shaft portion, and the shaft portion with an adjustment mechanism of an oral gag.

5 Claims, 3 Drawing Sheets

(56) References Cited

OTHER PUBLICATIONS

Hern, et al. "The Laryngeal Mask Airway in Tonsillectomy: The Surgeon's Perspective," Clinical Otolaryngol, 24, 122-125, Dec. 2, 1998.
Kanniah "Letter to the Editor Laryngeal Mask Airway and Tonsillectomy," International Anesthesia Research Society, vol. 103, No. 4, Oct. 2006.
Hamilton, et al. "Letter to the Editor Laryngeal Mask Airway and Tonsillectomy: A Question of Training," Anesthesia & Analgesia, vol. 104, No. 5, May 2007.
Agrawal, et al., "Modified Palate Mouth Gag Tongue Blade to Prevent Endotrachael Tube Compression," Plastic and Reconstructive Surgery, 857-859, Sep. 2005.
Mai, et al. "Basics of Pediatric Airway Anatomy, Physiology and Management," Boston University Medical Center, Department of Anesthesiology, Apr. 15, 2010.
V. Mueller and Snowden-Pencer Catalog, Ring Reactor Blades, internet http://www.cardinal.com/legacy/vmueller/vmcatalog/vmueller.html, printed May 26, 2010.
Medword Medical Sales, Surgical Instruments Images & Names: Oral & Tonsil Instruments, Internet http://www.medword.com/surgical/oti.html, printed Feb. 17, 2011.
Nucleus Catalog, "Placement of Endotrachael Tub and Nasogastric Tube," Internet http://catalog.nucleusine.com/enlargeexhibit.php?ID=8203&TC=&A=2, printed May 11, 2010, 1999.
Smiths Medical International Ltd., "Tracheal Tubes—A Guide to Size and Length" 2009.
LMA North America Inc., LMA Quick Reference, LMA, Sep. 2004.
Mouth Gags ORSupply.com, Mouth Gags Supplies, Internet http://www.orsupply.com/medical/surgical-instrument/Mouth-Gags/226, printed May 11, 2010.
Anecare, The QED-100 Use With the Laryngeal Mask Airway, Internet http://www.anecare.com/Products/QED-LMA-brief.html, printed May 11, 2010.
EP.Yimg.Com, Internet: http://ep.yimg.com/ca/1/yhst-35027408084415__2140-24840654, printed Feb. 17, 2011.
Express Surgical, Internet: http://www.expresssurgical.com/Resources/Images/Products/Large/171-001.jpg, printed Feb. 27, 2011.

\* cited by examiner

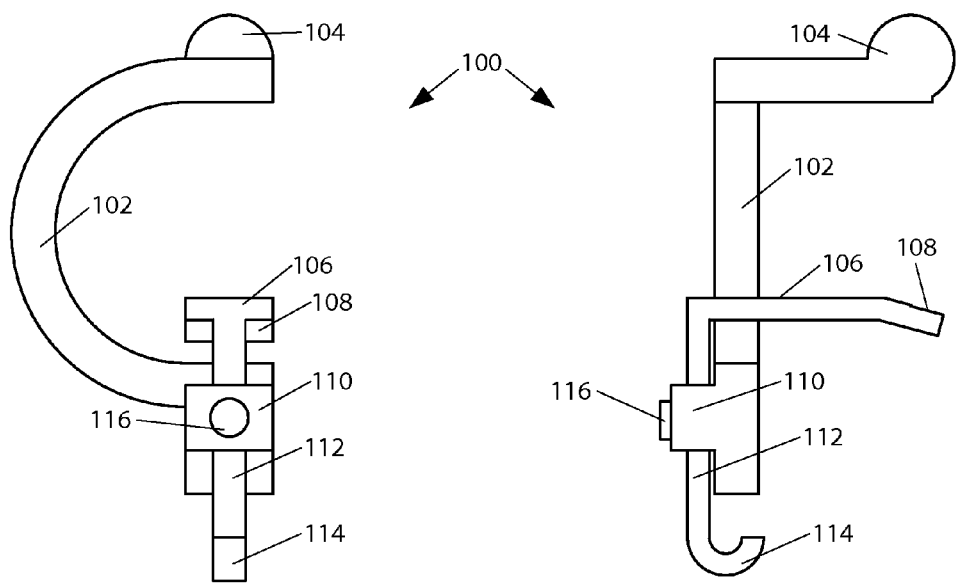
FIG. 1
PRIOR ART
FIG. 2
PRIOR ART
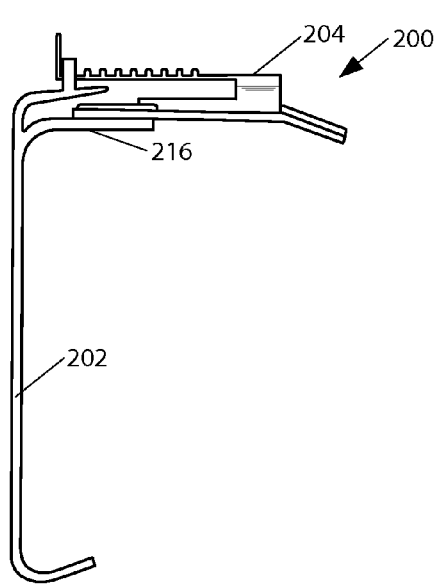
FIG. 3
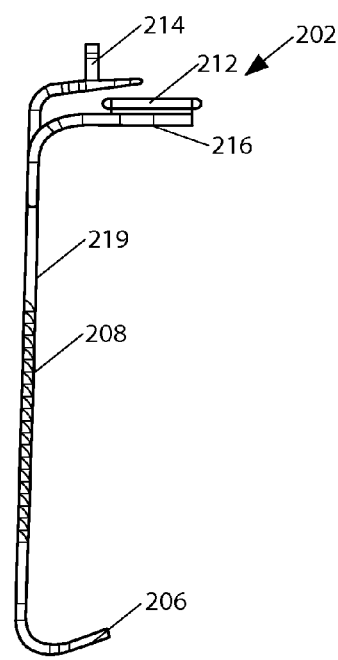
FIG. 4

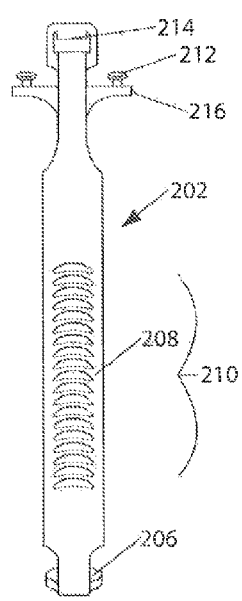
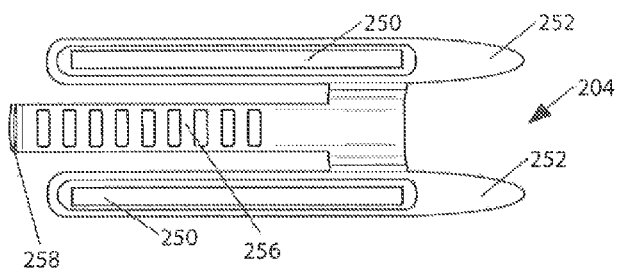
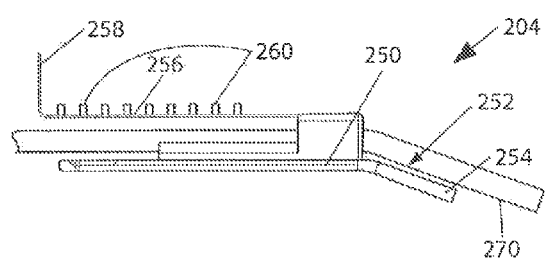
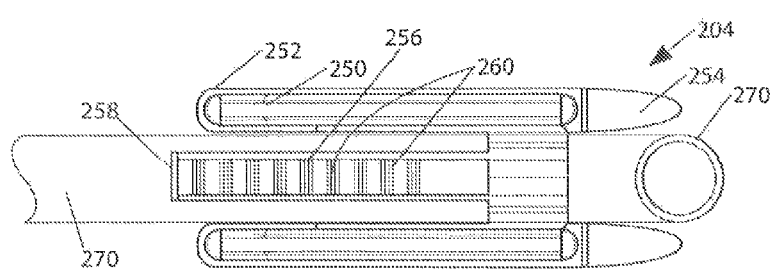
FIG. 5
FIG. 6
FIG. 7
FIG. 8

ADJUSTABLE TONGUE-POSITIONING DEVICE FOR SURGICAL GAG

RELATED APPLICATION

This application claim priority to U.S. Patent Application Ser. No. 61/602,947, filed Feb. 24, 2012, the disclosure of which is incorporated herein by reference.

BACKGROUND

When people are anesthetized, they are unable to control their jaws or tongues because the tongue is a voluntary muscle innervated by the then-somnolent brain. Tongue position in particular can be of importance during anesthesia because if it is allowed to fall backwards it can block the pharynx, impeding airflow, or it may obstruct access for intended surgical procedures on structures, such as tonsils and vocal chords, located in the pharynx or larynx.

Devices have been marketed for controlling tongue position of anesthetized subjects during surgery. These devices, known herein as oral gags, typically also have provisions for wedging open a patient's mouth for oral examination or surgical procedures. Most oral gags include a tongue-controller portion that serves both to restrain the patient's tongue during the procedure and, in some devices, to position an endotracheal tube for anesthesia. Some, such as the well-known McIvor include multiple tongue depressors in varying sizes to fit small children to adult. This requires the physician to select the appropriately sized depressor prior to surgery. Other manufacturers provide an oral gag and associated single size tongue depressor, or tongue positioning device, which either fits the subject or does not. These include the Bosworth, Tobold and Andrews depressors.

Oral gag devices are occasionally used with an endotracheal tube to permit a subject to breathe, or an anesthesiologist to ventilate the subject. Typical adult endotracheal tubes have outer diameters ranging from 10.2 to 13 millimeters, with pediatric tubes ranging from 6.2 to 11 millimeters in diameter, depending on tube length. Some sizes of laryngeal mask airways have oral tubes with diameters of 13 to 16 millimeters; for some patients, laryngeal mask airway oral tubes are sufficiently large in diameter that they cannot be used with typical existing oral gag devices because the oral gag device does not leave sufficient room for the tube. Some other prior devices may leave insufficient room for simultaneous presence of a laryngeal mask tube and surgical access to the mouth and pharynx.

Typically, a prior-art oral gag device 100 (FIG. 1 and FIG. 2) includes a rigid frame 102. Attached to the frame is typically an upper blade 104 with a smooth-sided surface for positioning at, and applying upward pressure to, the roof of a subject's mouth, and an attaching portion 110 for supporting a tongue positioning device 106. The device illustrated in FIG. 1 and FIG. 2 is not representative of any particular oral gag, it is intended to illustrate typical components and to illustrate the field of application of the device disclosed herein. Engagement between attaching portion 110 and tongue positioning device 106 is typically adjustable, by pressure applied to an engagement release 116, to allow adjustment of a displacement between the upper blade and tongue positioning device 106. The tongue positioning device 106 typically has a depressed tip 108, a vertical portion 112 with engaging notches, slots, or grooves for engagement with an engagement mechanism associated with engagement release 116, and a handle tab 114. In use, the upper blade 104 and tongue positioning 106 devices are placed within a subject's mouth, the engagement release 116 is pressed, and the handle tab 114 is pulled to tighten the tongue positioning device against the subject's lower jaw and tongue. The engagement release is then released to retain position with the subject's mouth open. Typical prior tongue positioning devices 106 are unitary components that are not adjustable. Particular prior-art oral gag devices may have tongue positioning devices 106 that may be easily interchanged with one having a different length, thereby better accommodating subjects having different mouth sizes.

SUMMARY

The proposed oral gag provides an oral gag with an adjustable vertical shaft component and a tongue depressor component that is adjustable in both height and length to accommodate the varying dimensions of patients' mouths ranging from small children to adults.

An adjustable tongue-positioning device for an oral gag device has a shaft portion with a vertical shaft adapted for slideably engaging with an oral gag device, an engagement bead attached to a support, the support attached to the vertical shaft, an engagement ring attached to the vertical shaft. The tongue positioning device also has an adjustable tongue portion with at least one tongue depressor portion having a slot adapted for engaging with the engagement bead of the shaft portion, and a springy ratchet adapted for engaging with the engagement ring of the shaft portion.

BRIEF DESCRIPTION OF THE DRAWINGS

FIG. 1 is a front-view illustration of a generic oral gag device.

FIG. 2 is a lateral view of the oral gag device of FIG. 1.

FIG. 3 is a lateral view of the present tongue positioning device for use in an oral gag device.

FIG. 4 is a lateral view of the shaft portion of the tongue positioning device of FIG. 3.

FIG. 5 is a front-view of the shaft portion of the tongue positioning device of FIG. 4.

FIG. 6 is a top view of the adjustable tongue portion of the tongue positioning device of FIG. 4.

FIG. 7 is a lateral view of the adjustable tongue portion of FIG. 6.

FIG. 8 is a line drawing illustrating the top view of the adjustable tongue portion of FIG. 6

DETAILED DESCRIPTION OF THE EMBODIMENTS

Figure 9:
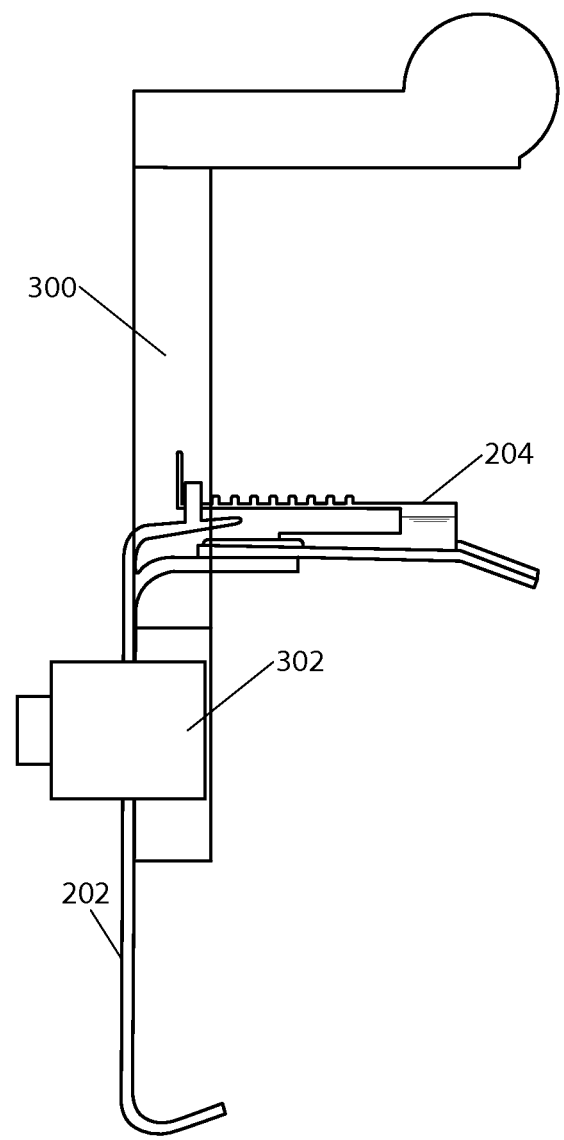
FIG. 9 is an oral gag assembly having the tongue positioning device of FIG. 3

The present adjustable oral gag has a tongue positioning portion 200, illustrated in FIG. 3, that is adjustable for the depth of a subject's mouth. Tongue positioning portion 200 has a shaft portion 202 and an adjustable tongue portion 204.

Shaft portion 202, also illustrated in FIG. 4 and FIG. 5, has a handle tab 206 for adjusting its position in a gag device resembling that of FIG. 9, and has slots 208 cut in a vertical shaft 210. Slots 208 are for engaging with an engagement mechanism 302 of an oral gag assembly 300 (FIG. 9). Shaft portion 202 also has engagement bead 212 on a support 216 for slideably engaging with a slot 250 (FIG. 6) in tongue depressor portion 252 of tongue portion 204, the support 216 for supporting adjustable tongue portion 204 and engagement bead 212 for applying force to the adjustable tongue portion. Shaft portion 202 also has an engagement ring 214 for engaging an adjustment ratchet 256 of the adjustable tongue portion. Support 216 and engagement ring 214 are attached to the shaft 210.

Adjustable tongue portion 204 preferably has two parallel tongue depressor portions 252, each of which has a turned-down tip 254 and a slot 250. The two parallel tongue depressor portions 252 are attached to a flexible or springy adjustment ratchet 256. It is understood that a unitary depressor may be used. Springy adjustment ratchet 256 has an operating tab 258 at an end opposite the turned-down tips 254 and is flexible along its length so that it may be depressed to selectively disengage ratchet teeth from retention members within the engagement ring.

Turned-down tips 254 of adjustable tongue portion 204 are spaced apart a distance greater than a diameter of a typical laryngeal mask airway tube 270 such that, if the adjustable tongue portion 204 is inserted deeply within a subject's pharynx, tips 254 will fit around airway tube 270. Further, since depth of insertion of the adjustable tongue portion 204 into a subject's pharynx is adjustable, interference of tongue portion 204 with many types of airways can be prevented.

Shaft portion 202 may be fabricated from any relatively stiff, biocompatible, material such as stainless steel or a stiff composite plastic. Adjustable tongue portion 204 may be fabricated from a springy stainless steel with an appropriately thin and springy adjustment ratchet 256, or may be fabricated from a springy plastic. Embodiments of the adjustable tongue portion fabricated from springy plastic may in some embodiments be disposable.

In operation, and as illustrated in FIGS. 3, 6 and 9, the slots 250 of adjustable tongue portion 204 are engaged with engagement beads 212 on supports 216, and operating tab 258 passed through engagement ring 214. The operating tab 258 is then depressed and the adjustment ratchet slides within adjustment ring 214 to adjust the tongue positioning portion to a length appropriate for a subject, and the tab is released thereby engaging the adjustment ring 214 with one or more of several teeth 260 along the surface of the adjustment ratchet 258. The vertical shaft 210 is slideably engaged with the engagement release device 302 of an oral gag 300, as best shown in FIG. 9.

Those skilled in the art will appreciate that the presently disclosed instrumentalities teach by way of example and not by limitation. Therefore, the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

What is claimed is:

1. An adjustable tongue-positioning device for an oral gag device comprising:
    a shaft portion comprising:
        a vertical shaft adapted for slideably engaging with the oral gag device,
        an engagement bead attached to a support, the support attached to the vertical shaft,
        an engagement ring attached to the vertical shaft; and
    an adjustable tongue portion comprising:
        at least one tongue depressor portion having a slot adapted for engaging with the engagement bead of the shaft portion, and
        a flexible ratchet adapted for engaging with the engagement ring of the shaft portion.

2. The adjustable tongue-positioning device of claim 1 comprising two spaced apart supports on the vertical shaft, each support having an engagement bead and wherein the tongue depressor portion has two spaced apart slots, each slot engaging one of the engagement beads on the supports so that the adjustable tongue support can be selectively positioned along the supports of the shaft portion.

3. The adjustable tongue-positioning device of claim 1 wherein the flexible ratchet is oriented above the tongue depressor portion to accommodate an endotracheal tube.

4. An adjustable tongue-positioning device for use with an oral gag comprising:
    a tongue depressor having at least one blade for engaging a tongue,
    a slot formed in the at least one blade,
    a ratchet portion positioned above the at least one blade to accommodate an endotracheal tube between the ratchet portion and the at least one blade; and
    the oral gag includes a verticle shaft comprising at least one support,
    an engagement bead mounted to at least one support, and an engagement ring;
    wherein the slot of the blade slidably engages with the engagement bead and the ratchet portion selectively engages the engagement ring and wherein the blade is slidable lateral the vertical shaft to adjust to different tongue sizes.

5. The device of claim 4 wherein at least one blade comprises two spaced apart blades with the ratchet portion positioned therebetween and the at least one support of the oral gag comprises two spaced-apart supports, each having an engagement bead for engaging the slots of the blades.

* * * * *